(12) United States Patent
Robb et al.

(10) Patent No.: US 6,579,703 B2
(45) Date of Patent: Jun. 17, 2003

(54) ENHANCED PROTEIN THERMOSTABILITY AND TEMPERATURE RESISTANCE

(75) Inventors: Frank T. Robb, Silver Spring, MD (US); Pongpan Laksanalamai, Baltimore, MD (US)

(73) Assignee: University of Maryland Biotechnology Institute, Baltimore, MD (US)

(*) Notice: Subject to any disclaimer, the term of this patent is extended or adjusted under 35 U.S.C. 154(b) by 0 days.

(21) Appl. No.: 09/835,909

(22) Filed: Apr. 16, 2001

(65) Prior Publication Data

US 2002/0077459 A1 Jun. 20, 2002

Related U.S. Application Data

(60) Provisional application No. 60/197,274, filed on Apr. 14, 2000.

(51) Int. Cl.[7] .................... C12D 19/34; C07K 14/00
(52) U.S. Cl. .................. 435/91.1; 435/6; 435/7.32; 435/71.1; 435/91.2; 530/350
(58) Field of Search .............. 530/350; 435/6, 435/91.1, 91.2, 7.32, 71.1

(56) References Cited

U.S. PATENT DOCUMENTS 5,474,892 A   12/1995   Jakob et al. ............... 435/4

OTHER PUBLICATIONS

Lee, et al., "Induction and regulation of heat–shock gene expression by an amino acid analog in soybean seedlings," Plant Physiol. (1996) 110: 241–246.

Jordano, "Tissue–specific expression of sunflower head shock proteins in response to water stress," The Plant Journal (1993) 4(6), 947–958.

Jordano, "Developmental and environmental concurrent expression of sunflower dry–seed–stored low–molecular–weight heat–shock protein and Lea mRNAs," Plant Molecular Biology, 19: 781–792, 1992.

Apuya et al., "Heat shock gene expression is controlled primarily at the translational level in carrot cells and somatic embryos," The Plant Cell, vol. 4, 657–665, Jun. 1992.

Zimmerman, et al., "Novel regulation of heat shock genes during carrot somatic embryo development," The Plant Cell, vol. 1, 1137–1146, Dec. 1989.

"Heat Shock Response," ed. Lutz Nover, Ph.D., CRC Press, 1991.

*Primary Examiner*—Kenneth R. Horlick
*Assistant Examiner*—Alexander H. Spiegler
(74) *Attorney, Agent, or Firm*—Steven J. Hultquist; Marianne Fuierer; Yongzhi Yang

(57) ABSTRACT

Small heat shock proteins, e.g., *Pyrococcus fuiosus* (Pfu-sHSP), confer thermotolerance on cellular cultures and on proteins in cellular extracts during prolonged incubation at elevated temperature, demonstrating the ability to protect cellular proteins and maintain cellular viability under heat stress conditions. Such heat shock proteins are effective to combat enzymatic aggregation and intracellular precipitation during heat stress, and thereby enable enhancement of the utility and stability of enzymes in various applications, e.g., Taq polymerase in PCR applications, digestive enzymes in microbial degradative applications, etc.

26 Claims, 8 Drawing Sheets

FIG.1

```
TCTTTTTGGAGTATTTTTGATTGTTCGGTAAATTCTACTCTTATCGAAAATATTTA
TAAACCCCAAATAATTTAATAACTAATGGTAACCAAAAGTGGGAGGGGTGAGAGAG
ATGGTGAGGAGAGAATAAGAAGATGGGACATATGGGATCCATTCGACCTAATAAGGGAA
 M  V  R  R  I  R  R  W  D  I  W  D  P  F  D  L  I  R  E
ATACAAGAGGAAATTGATGCAATGTTCGATGAATTCTTCAGCAGGCCAAGGCTCTGG
 I  Q  E  E  I  D  A  M  F  D  E  F  F  S  R  P  R  L  W
ACTTACAGAGAAGTGGAGCGAGCCAATGTATGAGGAGAGTAGGAGAAGTCTGG
 T  Y  R  R  W  S  E  P  A  M  Y  E  E  R  V  G  E  V  W
AGAGAGCCATTCGTTGATATCTTTGACAACGGAGATGAGTTTGTAATCACGGCAGAG
 R  E  P  F  V  D  I  F  D  N  G  D  E  F  V  I  T  A  E
CTTCCAGGAGTGAGAAGAAGACATCAAAGTGAGGGTTACAGAGGATACAGTATAC
 L  P  G  V  R  K  E  D  I  K  V  R  V  T  E  D  T  V  Y
ATTGAGGCCACAGTTAAGAGGAGAAGAATTAGAAGAGAAGGAGCAGTGAGAATA
 I  E  A  T  V  K  R  E  K  E  L  E  R  E  G  A  V  R  I
GAGAGATACTTTACAGGGTATAGAAGAGCCATCAGGCTTCCAGAAGAAGTTATTCCA
 E  R  Y  F  T  G  Y  R  R  A  I  R  L  P  E  E  V  I  P
GAGAAGGCAAAGGCCAAGTACAACGGAGTGCTTGAGATCAGAGTTCCAAAGAAG
 E  K  A  K  A  K  Y  N  N  G  V  L  E  I  R  V  P  K  K
CACCCAACAAAGAAGGAGAGTGAAGGATTCGAAGTTAAAGTTGAATAGCTTTAGTAC
 H  P  T  K  K  E  S  E  G  F  E  V  K  V  E
CCTTCTTTCTTGATTATTGGAAATATTTTGGAGGTATTGGTTCTATTATCAATTA
ATTCCTTTTATTTTAAAATCCCTTGGATC
```

ENHANCED PROTEIN THERMOSTABILITY AND TEMPERATURE RESISTANCE

CROSS-REFERENCE TO RELATED APPLICATION

The priority of U.S. Provisional Patent Application No. 60/197,274 filed Apr. 14, 2000 in the names of Frank T. Robb and Pongpan Laksanalami for "Enhanced Protein Thermostability and Temperature Resistance" is hereby claimed.

GOVERNMENT RIGHTS IN INVENTION

Work relating to the present invention was performed during the performance of Grant No. 98-0935. The United States Government has certain rights in the invention.

BACKGROUND OF THE INVENTION

1. Field of the Invention

The present invention generally relates to a heat shock protein from *Pyrococcus furiosus,* to a method of protecting and extending the durability of a recombinant DNA polymerase, and to a PCR kit.

2. Description of the Related Art

All organisms respond to elevated temperature by specifically inducing the expression of a set of new proteins, termed "heat shock proteins" or "HSPs." Although this response has been known for over thirty years, the specific role of individual HSPs in the overall response is still largely unknown. The HSPs to which functional character has been attributed have been characterized as molecular chaperones that enable protein folding, preventing denaturation of other proteins, or mediating proteolysis. This role, however, has only been demonstrated for a few of the many known HSPs and the function of other HSPs remains unknown. Moreover, it is not known which of the HSPs are essentials for the overall shock response except in the cases described below.

All organisms have a basal level of thermotolerance that is an organism-specific temperature threshold above which the organisms die. Basal levels of thermotolerance are probably determined by a variety of factors, including, for example, membrane composition and the innate thermal stability of enzymes involved in normal cellular processes. An additional level of thermotolerance can be acquired by exposure of an organism to sublethal processes. Such "acquired thermotolerance" is believed to result from the production of HSPs in response to the sublethal high temperature exposure.

HSPs have been categorized by size and DNA sequence into families that are evolutionarily conserved. These families include the HSP 100, HSP 90, HSP 70, the HSP 60 and a variable class of low molecular weight proteins that range from 12–42 kDa. The HSPs found in this class of low molecular weight proteins are referred to as small heat shock proteins or sHSPs. In animals, this class of low molecular weight proteins ranges from 20–25 kDA. In the plant kingdom, the corresponding range is 14–20 kDa.

All of the low molecular weight HSPs are distinguished by conserved carboxy termini that are highly homologous to the αB-crystallin structural protein of the eye lens. αB-crystallin is itself capable of acting as a molecular chaperone, and all sHSPs have been demonstrated to exhibit chaperone activities in in vitro experiments. Their role in cells has not yet been demonstrated.

While it might be assumed that the HSPs play a role in thermotolerance because of the correlation of their abundant synthesis with exposure to increased temperature, earlier work with yeast had suggested that they are unimportant for the development of thermotolerance, as elimination of a single yeast sHSP had no effect on thermotolerance. In addition, in Drosophilia cells, the use of antisense technology caused a specific decrease in the synthesis of the sHSP 26 protein, but such decrease had no effect on thermotolerance.

In addition to being induced by temperature stress, many HSPs, including those in the sHSP class, can be induced by other stresses such as exposure to arsenite, ethanol, heavy metals, amino acid analogs (Lee, Y. R., et al., Plant Physio. 110:241–48 (1996); and Nover, L., (ed.) Heat Shock Response, CRC Press (1990)) and water stress (Almoguera, C., et al., The Plant Journal 4(6): 947–58 (1993). In addition, increasing numbers of HSPs and HSP homologs are found to be regulated in developmental and tissue-specific ways (see, e.g., Almoguera, C. and J. Jordano, Plant Molecular Biol. 19:781–92 (1992); Apuya, N. R. and J. L. Zimmerman, The Plant Cell, 4:657–65 (1992); Cordewener, J. H. G., et al., Plant Cell 1:1137–1140 (1989). Proteins with highly conserved sequences related to HSPs, HSP cognates, may be expressed in non-stressed normal cells, but are not induced by thermal stress.

The mechanisms of action for the small HSPs are not clearly understood at present. There is a need for a better understanding of sHSPs despite other recombinant archael sHSPs that have been overexpressed in *E. coli.*

The present invention embodies an advance in the field of sHSPs that correlatively advances the understanding of the mechanism of sHSPs.

SUMMARY OF THE INVENTION

The invention relates to heat shock proteins and their methods of use.

In one aspect, the invention relates to a purified and isolated nucleic acid sequence encoding a heat shock protein comprising SEQ ID NO. 1.

Another aspect of the invention relates to the protein encoded by the nucleic acid comprising SEQ ID NO. 1, and to compositions comprising same.

Another aspect of the invention relates to a protein comprising the amino acid sequence of SEQ ID NO. 2, and to compositions comprising same.

A still further aspect of the invention relates to a method of protecting and extending the durability of a recombinant DNA polymerase, comprising the steps of:

purifying a low molecular weight heat shock protein;

adding the heat shock protein to a buffer solution containing the polymerase;

incubating the solution at extended temperature for extended time;

adding components necessary for PCR;

thermocycling the reaction to produce product from amplification of genomic deoxyribonucleic acid; and examining the product of the reaction by gel electrophoresis.

Yet another aspect of the invention relates to a method of maintaining proteins in solution, comprising the steps of:

adding a low molecular weight heat shock protein to the solution;

elevating the temperature of the solution; and measuring the enzymatic activity by absorbance.

A still further aspect of the invention relates to a PCR kit comprising the protein encoded by the nucleic acid comprising SEQ ID NO. 1, or the protein comprising the amino acid sequence of SEQ ID NO. 2, and one or more other PCR reagents.

In a further compositional aspect, the invention relates to a composition comprising (i) a biological component and (ii) an HSP or a precursor thereof, which is (A) exogenous to the biological component, and (B) thermostabilizingly effective for the biological component in the composition.

The invention contemplates in various further aspects:
a method of enhancing the stability of Taq polymerase in a PCR operation, by conducting the PCR operation in the presence of a HSP;
a PCR kit including PCR primers, Taq polymerase, deoxyribonucleoside triphosphates and an HSP;
transformed cells capable of expressing Pfu-sHSP;
recombinant DNA vectors for expression of Pfu-sHSP; and
a method of stabilizing a protein solution, including a first protein therein, against heat-mediated agglomeration of the first protein in the solution, by incorporating in the solution a heat shock protein that is non-endogenous with respect to the first protein.

Other aspects, features and embodiments of the invention will be more fully apparent from the ensuing disclosure and appended claims.

BRIEF DESCRIPTION OF THE DRAWINGS

FIG. 1 is the nucleotide sequence (SEQ ID NO. 1; GenBank Accession No. AF 256212) and the amino acid sequence (SEQ ID NO. 2; GenBank Accession No. AF 256212) of *Pyrococcus furiosus* heat shock protein.

DETAILED DESCRIPTION AND PREFERRED EMBODIMENTS OF THE INVENTION

Figure 2:
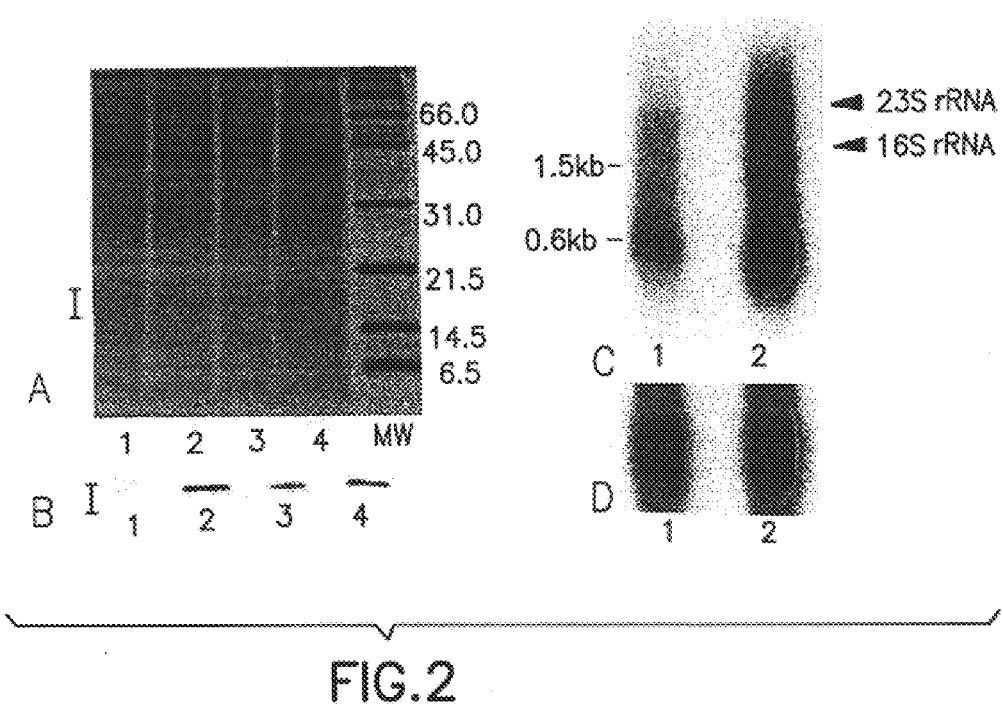
FIG. 2 demonstrates the SDS PAGE (15%) and blot analysis of Pfu-sHSP.

Relative to the present invention and its features, aspects and embodiments as more fully described hereinafter, the disclosure of U.S. Provisional Patent Application No. 60/197,274 is hereby incorporated herein by reference in its entirety.

Definitions

As used herein, the following terms have the following meanings.

As used herein, the term "heat shock protein" refers to any protein whose synthesis is enhanced when an organism or its cells are exposed to an increased temperature for that species; typically a temperature increase in a range of from about 5 to about 15° C.

As used herein, the term "low molecular weight heat shock protein" refers to those heat shock proteins that are between 12–42 kilodaltons (kDa) in size.

As used herein, the term "sHSP 20" refers to the small heat shock proteins encoded by SEQ ID NO. 1.

As used herein, the term "thermotolerance" refers to the ability of a cell to survive exposure to temperatures above its normal growth temperature.

As used herein, the term "basal thermotolerance" refers to the maximum temperature to which an organism or cell can survive when the shift to that temperature is rapid.

As used herein, the term "acquired thermotolerance" refers to the increase in thermotolerance that results from a prior (pre) exposure to a sublethal heat shock temperature.

As used herein, the term "transgenic cell line" or "transgenic culture" refers to a cell or culture that has stably incorporated added DNA sequences into its genome after deliberate introduction of DNA into that cell.

As used herein, the term "DNA molecule" refers to the polymeric form of deoxyribonucleotides (adenine, guanine, thymine or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids and chromosomes.

As used herein, the term "vector" refers to a replicon, such as a plasmid, phage, cosmid or virus to which another DNA or RNA segment may be attached so as to bring about the replication of the attached segment. Specialized vectors were used herein, containing various promoters, polyadenylation signals, genes for selection, etc.

As used herein, the term "transcriptional and translational control sequences" refer to DNA regulatory sequences, such as promoters, enhancers, polyadenylation signals, terminators, and the like, that provide for the expression of a coding sequence in a host cell.

As used herein, the term "promotor sequence" is a DNA regulatory region capable of binding RNA polymerase in a cell and initiating transcription of a downstream (3' direction) coding sequence. Eukaryotic promoters will often, but not always, contain "TATA" boxes and "CAT" boxes. Prokaryotic promoters contain Shine-Dalgarno sequences in addition to the −10 and −35 consensus sequences.

As used herein, the term "selection gene" refers to a gene that enables the discrimination of cells displaying a required phenotype upon implementation of certain conditions. For example, the growth of bacteria in a medium containing antibiotics to select for the bacterial cells containing antibiotic resistance genes.

As used herein, the terms "restriction endonucleases" and "restriction enzymes" refer to bacterial enzymes, each of which cuts double-stranded DNA at or near a specific nucleotide sequence.

As used herein, the terms "transformed" or "transfected" by exogenous or heterogenous DNA when such DNA has been introduced inside the cell. The transforming DNA may or may not be integrated (covalently linked) into the genome of the cell. In prokaryotes, yeast and mammalian cells, for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones of a population of daughter cells containing the transforming DNA.

As used herein, the term "clone" refers to a population of cells derived from a single cell or common ancestor by mitosis.

As used herein, the term "cell line" is a clone of a primary cell that is capable of stable growth in vitro for many generations.

In accordance with the present invention, conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells & Enzymes," IRL Press (1986); "A Practical Guide to Molecular Cloning," B. Perbal (1984).

In a further aspect of the invention, the reagents described herein can be packaged in a kit form for carrying out PCR. As used herein, the term "package" refers to a solid matrix or materials customarily utilized in such a kit system in the form of at least one or more enclosure that is capable of holding within fixed limits at least one or more of the reagent components for use in PCR. Such materials include glass and plastic (e.g., polyethylene, polypropylene, and polycarbonate) bottle, vials, paper, plastic, plastic-foil laminated envelopes and the like. Thus, for example, a package can be a glass vial used to contain the appropriate quantities of polynucleotide primer(s), genomic DNA, vectors and DNA polymerase or a combination thereof, in addition to an appropriate amount of sHSP. An aliquot of each component sufficient to perform at least one complete PCR procedure is provided in each package.

Kits useful for producing a primer extension product for amplification of a specific nucleic acid sequence using a primer extension reaction methodology also typically includes, in separate container within the kit, dNTPs where N is adenine, thymine, guanine and cytosine and other like agents for performing primer extension reactions.

The reagent species of any system described herein can be provided in solution, as a liquid dispersion or as a substantively dry powder, e.g., the primers may be provided in lyophilized form.

The advantage of using a small heat shock protein to prevent the aggregation of mixtures of proteins is clear, but using a recombinant protein comprising a small heat shock protein was demonstrated by the inventors hereof to extend the half-life of a pure enzyme in vitro. At a temperature that was higher than the optimal temperature and Tmax of the enzyme, the inventors hereof demonstrated that the half-life of the enzyme incubated with the recombinant protein was increased approximately four-fold compared to the enzyme control alone.

The heat shock proteins of the invention, *Pyrococcus fuiosus* (Pfu-sHSP), confer thermotolerance on cellular cultures and on proteins in cellular extracts during prolonged incubation at elevated temperature, demonstrating the ability to protect cellular proteins and maintain cellular viability under heat stress conditions. Such heat shock proteins are effective to combat enzymatic aggregation and intracellular precipitation during heat stress, and thereby enable enhancement of the utility and stability of enzymes in various applications, e.g., Taq polymerase in PCR applications, digestive enzymes in microbial degradative applications, etc.

The cytoprotective character of the heat shock proteins of the invention also enables the commercial exploitation of correspondingly transformed cellular cultures for elevated temperature fermentation and microbial culturing operations that take advantage of improved kinetics associated with higher temperature processing regimes. Such cytoprotective character further facilitates clinical applications in which heat-mediated undesirable side effects of pyrogenic therapeutic agents, thermal treatments and environmental exposure are combated by administration of heat shock proteins of the invention to a human or animal patient in need thereof (or by gene therapy producing in vivo expression of such cytoprotective proteins).

The present invention comprehends a composition comprising (i) a biological component and (ii) an HSP or a precursor thereof, which is (A) exogenous to the biological component, and (B) thermostabilizingly effective for the biological component in the composition.

The invention also contemplates enhancing the stability of Taq polymerase in a PCR operation, by conducting the PCR operation in the presence of a HSP. The PCR operation may be carried out with the provision of a PCR kit including PCR primers, Taq polymerase, deoxyribonucleoside triphosphates and an HSP according to the present invention.

Transformed cells capable of expressing Pfu-sHSP may be readily formed and utilized to produce Pfu-sHSP for various applications of the invention, e.g., by use of recombinant DNA vectors for expression of Pfu-sHSP. The resulting heat shock protein then may be employed for stabilizing a protein solution, including a first protein therein, against heat-mediated agglomeration of such first protein in the solution, by incorporating in the solution the Pfu-sHSP or other heat shock protein that is non-endogenous with respect to the first protein.

The small heat shock protein from *Pyrococcus furiosus* (Pfu-sHSP) is composed of 167 amino acid residues encoded by an ORF of 504 nucleotides (GenBank Accession number AF256212).

The invention is described more specifically hereinafter, in respect of the present inventors' work involving the gene encoding the small heat shock protein (sHSP) from the hyperthermophile *Pyrococcus furiosus,* as cloned and overexpressed in *E. coli.* The sHSP gene was found to be inducible by heat shock at 105° C. In specific experminents, recombinant sHSP prevented the majority of *E. coli* proteins from aggregating in vitro for up to 40 minutes at 105° C., and also prevented bovine glutamate dehydrogenase from aggregating at 56° C. Survivability of *E. coli* overexpressing the sHSP was empirically determined to be enhanced approximately 6-fold during exposure to 50° C. for 2 hours compared with a control culture which was not expressing sHSP. These results evidence the utility of heat shock proteins from hyperthermophiles in conferring a survival advantage on mesophilic bacteria by preventing protein aggregation at supraoptimal temperatures, and implicate usages of such heat shock proteins in microbial culturing, fermentation, and numerous other bioprocessing applications.

While the ensuing description is directed illustratively to small heat shock proteins (sHSP) of *Pyrococcus furiosus,* it is to be recognized that the utility of the present invention is not thus limited and that a wide variety of other sHSPs may be employed in accordance with the present invention. Examples include, without limitation, sHSPs from *P. horikoshii* and *Aquifex aeolicus.*

Accordingly, the features and advantages of the invention are more fully apparent from the following illustrative examples, which are not intended in any way to be limitingly construed, as regards the invention hereinafter claimed.

EXAMPLE 1

Cloning, Overexpression and Purification of the Recombinant Protein

The region encoding the Pfu-shsp gene (SEQ ID NO. 1; GenBank Accession No. AF 256212) (FIG. 1) was amplified from *Pryrococcus furiosus* genomic DNA by PCR using two primers: Pfu-shspN with an NcoI site (underlined) (5'G CCATGGTGAGGAGAATAAGAAGATGG) (SEQ ID NO. 3) and Pfu-shspC with an XhoI site (underlined) (5'A CTCGAGCTATTCAACTTTAACTTCGAATCCTTC) (SEQ ID NO. 4).

The amplified ORF was cloned into the pCR Zero Blunt vector (Invitrogen, Carlsbad, Calif.). The insert was digested by NcoI and XhoI and then subcloned into the isopropyl-1-thio-β-D-galacto-pyranoside (IPTG)-inducible pET19b expression vector (Novagen, Madison, Wis.) designated pPfu-shsp. The *E. coli* strain BL21(DE3) (Novagen, Madison, Wis.) carrying pSJS1240 which encodes rare tRNAs for leu and arg in *E. coli* (Kim et al. 1998d) was used as an expression host. *E. coli* cells carrying these 2 plasmids were grown in Luria-Bertani broth containing 50 μg/ml ampicillin and spectinomycin to an $A_{595}$ of 0.6.

The Pfu-sHSP expression was induced by 1 mM isopropyl-1-thio-β-D-galacgtopyranoside (IPTG) for 3 hours. The same strain carrying pET19b and pSJS 1240 served as a control. SDS PAGE of *E. coli* overexpressing Pfu-sHSP crude extract reveals an additional protein of 20 kDa in size which corresponds to the protein molecular weight deduced from the predicted amino acid sequence. After induction, cells overexpressing Pfu-sHSP were harvested and resuspended in 25 mM potassium phosphate buffer, pH 7.0, 2 mM DTT, 1 mM EDTA (buffer A). The cells were disrupted using a French Press (SLM instrument, Urbana, Ill.) at 16,000 psi and centrifuged at 5000× g for 15 minutes.

Pfu-sHSP appeared in a pellet fraction as indicated by SDS PAGE. The pellet then was dissolved in buffer A by heating at 85° C. for 20 minutes. The dissolved pellet was filtered and loaded onto an anion exchange column (MonoQ, Pharmacia Biotech, Uppsala, Sweden) previously equilibrated with buffer A. The Pfu-sHSP was eluted using an NaCl gradient, at 0.35 M NaCl. The fractions were pooled and concentrated, and the protein appeared homogeneous by SDS PAGE electrophoresis visualized with silver stain.

Rabbit polyclonal antibody preparations against the Pfu-sHSP were obtained by immunization of a rabbit with the purified, recombinant Pfu-sHSP (Bio-world, Dublin, Ohio).

The Pfu-sHSP, containing 167 amino acid residues, was overexpressed in *E. coli*. The SDS PAGE revealed that the molecular weight monomeric Pfu-sHSP was 20 kDa. The amino acid sequence of this recombinant protein is shown in FIG. 1 (SEQ ID NO. 2) (GenBank Accession No. AF256212).

The purified Pfu-sHSP was used throughout the experiments.

EXAMPLE 2

Induction of the Small Heat Shock Protein

*Pyrococcus furiosus* was grown as described elsewhere (Gonzalez et al., 1998) at 95° C. for 3 hours and then shifted to 104° C. for 2 hours. The cells were collected and frozen immediately and Western blot analysis was performed (Sambrook et al., 1989) to monitor the Pfu-sHSP induction.

The 104° C. temperature is considered a heat shock temperature for *Pyrococcus furiosus* at which it grows optimally at 103° C. The control culture continued growing at 95° C. without shifting to 104° C. for another 2 hours. A strong signal was observed in the 2-hour heat shocked cells whereas there was no signal observed in the non-heat shocked culture. This indicated that native Pfu-sHSP is heat-inducible, and the protein is not synthesized at subinhibitory growth temperatures.

FIG. 2 shows the SDS PAGE (15%) and the Western blot analysis of the recombinant and the native Psf-sHSP.

Specifically, *Pyrococcus furiosus* was cultured in a modified 20L fermentor (New Brunswick) or in with $S^0$ in the medium without maltose (Adams, M. W. W. 1995. Large-scale growth of hyperthermophiles, p. 47–49. In F. T. Robb (ed.) and A. R. Place. Archaea, a laboratory manual, thermophiles. Cold Spring Harbor Laboratory Press, Plainview, N.Y.). The cultures were incubated at 95° C. for 4 hours, then shifted to 105° C. for 0, 30, 60, 120 minutes before chilling on ice and harvesting by centrifugation at 7,500× g for 15 minutes. The total protein of the cell extracts were measured and an equal amount of protein was loaded onto each lane of an SDS gel. Western blot analysis was conducted. A strong signal at 20 kDa was observed in lanes 2–4, corresponding to 30, 60, and 120 minutes after onset of heat shock whereas no signal was observed in lane 1 corresponding to the non-heat shocked control culture. This indicated that native Pfu-sHSP was strictly heat-inducible, and that protein was not required for rapid growth at the optimal growth temperature.

The expression of mRNA was measured from the gene encoding the Pfu-sHSP under heat shock conditions using Northern blot analysis. Total RNA was isolated from *P. furiosus* after exposure to 105° C. for 120 minutes, compared to the non-heat shocked control culture. Total RNA (4 μg) was electrophoresed on a 1.5% agarose gel for Northern blot analysis using the radiolabelled PCR probe generated by PCR amplification from primers Pfu-shspN and Pfu-shspC using $^{32}P$ labeled dCTP. Hubridization with this probe revealed a transcript of 600 nucleotides corresponding to the size of the putative Pfu-sHSP gene. A radiolabelled probe from the gene encoding *P. furiosus* glutamate dehydrogenase, which is expressed constitutively, was used as a control.

EXAMPLE 3

Protection of *E. coli* Proteins and Cell Viability Under Heat Stress

*E. coli* strains containing either pPfu-sHSP or pET19b were induced as described above. The total protection concentration was determined using the Bradford protein assay kit (BioRad, Hercules, Calif.). The total proteins in crude extract were diluted in buffer A to a concentration of 4 mg/ml. The crude extract of each sample was covered with mineral oil and heated at 105° C. for 0, 20, 30 and 40 minutes. After cooling down at room temperature, the samples were centrifuged at 10,000× g for 5 minutes and the supernatants were collected.

The soluble proteins were visualized by SDS PAGE (Sambrook et al., 1989).

The induced cells were also tested for survivability at 50° C. The cultures were shifted rapidly to 50° C. in a water-bath shaker. Samples were taken at 0, 20, 40, 60 and 120 minutes. Samples of the culture were diluted at each time point and plated on Lutria-Bertani agar containing 50 μg/ml of ampicillin and spectinomycin. Cell viability was determined by counting the colony-forming units after overnight incubation.

The capacity for Pfu-sHSP to stabilize the full complement of soluble proteins in E. coli cell free extracts was determined. All of the proteins that can be detected by SDS PAGE in E. coli extracts containing overexpressed Pfu-sHSP remained soluble after heat treatment at 105° C., and were recovered in the supernatent fraction after centrifugation. The Bradford protein assay indicated that the total protein concentration in the supernatent of the control decreased approximately 50% whereas those in supernatent with the presence of Pfu-sHSP decreased only 5%.

Figure 3:
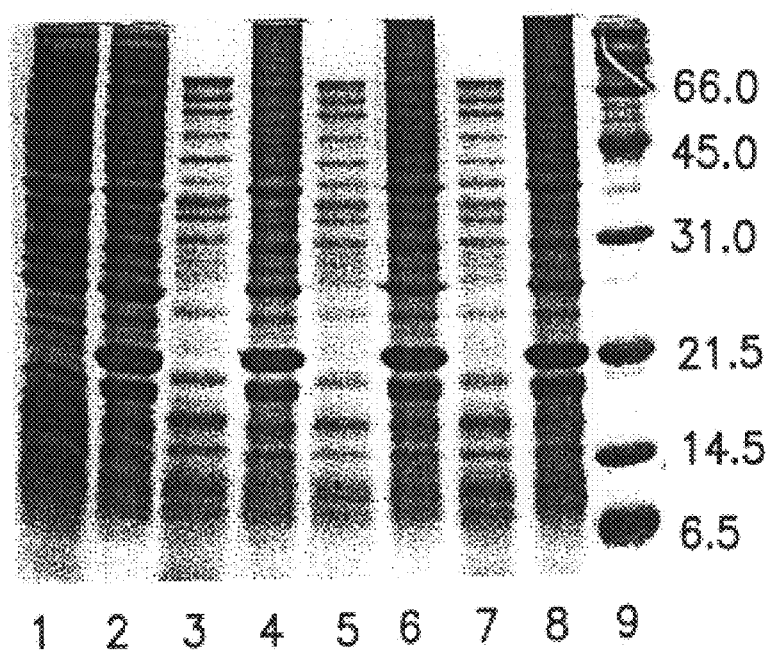
FIG. 3 demonstrates the SDS PAGE (15%) analysis of thermal protection of *E. coli* crude extract by *Pyrococcus furiosus*-sHSP at 105° C.

FIG. 3 shows the SDS PAGE (15%) analysis of the thermal protection of E. coli crude extract by Pfu-sHSP at 105° C.

As the Pfu-sHSP is capable of protecting E. coli proteins from aggregation in vitro, the issue of whether the Pfu-sHSP could protect cell viability was addressed. The E. coli culture overexpressing Pfu-sHSP and a control E. coli culture with pET vector and no insert were incubated at 50° C. for 2 hours, while viability was measured. The single order death rate of E. coli overexpressing Pfu-sHSP was approximately 6–7 fold lower than that of the culture transformed with pET19b and pSJS1240. The difference in viability between protected and unprotected cells after 120 minutes at 50° C. was approximately 3 orders of magnitude. See Table 1 in respect of the reduction of death rate at 50° C. of the E. coli overexpressing Pfu-sHSP in vivo.

TABLE 1

Death rate of E. coli overexpressing Pfu-sHSP

| E. coli BL21 (DE3) | Death rate (log CFU/100 µl/min) |
|---|---|
| PET19b/pSJS1240 | 0.0058 |
| PPfu-sHSP/pSJS1240 | 0.038 |

EXAMPLE 4
Glutamate Dehydrogenase Activity Assays

Bovine glutamate dehydrogenase (boGDH) (Sigma, Milwaukee, Wis.) was diluted in EPPS buffer, pH 7.5 to a concentration of 0.9 mg/ml to yield an initial rate of $\Delta A=0.06$/minute. The enzyme was incubated at 56° C. with 2.25 mg/ml of the purified Pfu-sHSP for various times. The samples were removed at 0, 2 and 4 minutes and then centrifuged at 10,000× g for 2 minutes. The supernatants were tested for the residual enzymatic activity following the method described previously (Robb et al., 1992). The residual activity of boGDH was determined using a Beckman DU640 spectrophotometer fitted with a temperature controller at 340 nm and 25° C. The assay mixture contained 100 mM EPPS pH 8.0, 65 mM glutamic acid and 16.25 mM NADP. There was no detectable GDH activity in the purified Pfu-sHSP.

The inventors hereof have found that the Pfu-sHSP can protect bovine GDH by aggregation prevention. As a small heat shock protein can prevent aggregation of mixtures of proteins, the inventors hereof tested the ability of the recombinant Pfu-sHSP to extend the half-life ($t_{1/2}$) of a pure enzyme in vitro. The mesophilic glutamate dehydrogenase from bovine (boGDH) (Sigma, Milwaukee, Wis.) was used as a model. The optimal temperature and Tmax of boGDH are 25° C. and 48° C., respectively. The purified Pfu-sHSP was used to protect boGDH under heat treatment at 56° C.

The control incubation was without Pfu-sHSP in the same buffer used to store the Pfu-sHSP. In addition, to confirm that the GDH activity was not from E. coli GDH that may possibly be a minor contaminant in the purified Pfu-sHSP resulting in increased GDH activity, the Pfu-sHSP preparation was assayed at high concentration for GDH activity using the same method. No GDH activity was detected in the purified Pfu-sHSP.

The $t_{1/2}$ of boGDH incubated with Pfu-sHSP at 56° C. was increased approximately four-fold compared to the boGDH control. See Table 2 for the results.

TABLE 2

Specific activity of boGDH at 56° C.

| GDH | Half-life (seconds) |
|---|---|
| GDH (0.9 mg/ml) | 38 |
| GDH/Pfu-sHSP (2.25 mg/ml) | 152 |

The inventors hereof examined the possibility that the activity of boGDH was protected as a result of prevention of aggregation by Pfu-sHSP. The absorbance ($A_{280}$) of the supernatent of boGDH solutions incubated at 56° C. with or without the presence of Pfu-sHSP was measured. The amount of precipitate had increased and the $A_{280}$ of boGDH without Pfu-sHSP was reduced dramatically whereas that of boGDH with Pfu-sHSP was not.

Figure 4:
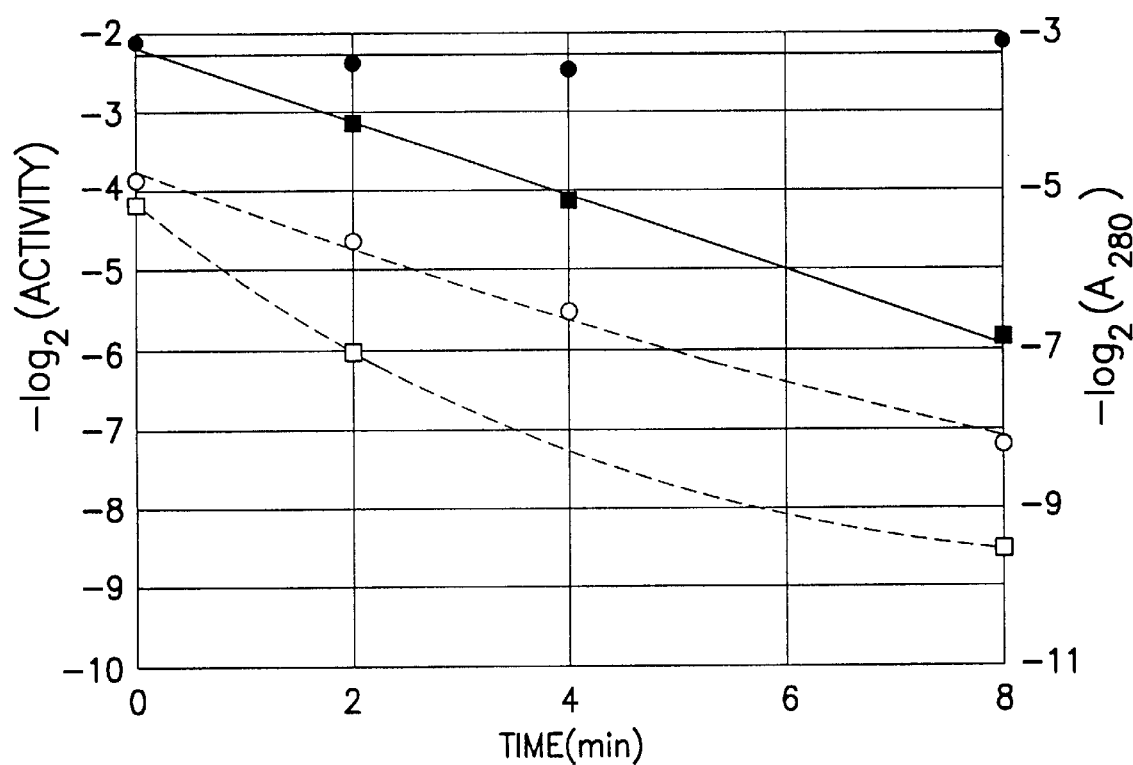
FIG. 4 is a graph of supernatant bovine glutamate dehydrogenase activity and $A_{280}$ values as a function of time.

In the experiment where boGDH was incubated alone, the apparent $t_{1/2}$ was approximately 2 minutes whereas the boGDH to which sHSP was added did not precipitate at all during the course of the experiment. The activity of the boGDH in the supernatants, on the other hand, declined in both cases, as shown in FIG. 4. Thus, much of the boGDH that remained in solution was denatured. In this case, the enzyme was maintained in solution but not preserved from denaturation. This is an important result that indicates that the probable mode of action of Pfu-sHSP is preventing non-specific aggregation of proteins thereby allowing them to be recruited to either refolding or protein turnover pathways.

EXAMPLE 5
DNA Polymerase Protection by Recombinant Protein 1.25 Taq Polymerase (Sigma, catalog number D1806) was incubated with and without 7.5 µg of Pfu-sHSP in 40 µl of Taq polymerase buffer with 15 mM $MgCl_2$ (Sigma) at −10 and 50° C. for 16 hours. PCR was done using the incubated Taq polymerase. The PCR reaction was carried out as follows:

1. 1× Taq polymerase buffer
2. 1 µM forward and reverse primers
3. 0.2 mM dNTP
4. 1.25U Taq polymerase The PCR cycles were carried out according to the following chart of cycles:

| Cycles | 1 cycle | 28 cycles | | | 1 cycle | |
|---|---|---|---|---|---|---|
| Temperature | 94° C. | 94° C. | 52° C. | 72° C. | 52° C. | 72° C. |
| Time | 2 minutes | 30 seconds | 30 seconds | 30 seconds | 2 minutes | 2 minutes |

The PCR products were visualized in 1% agarose gel electrophoresis.

Taq polymerase was incubated with sHSP at 50° C. for 20 hours. PCR of a target containing the gene encoding sHSP was performed using Pfu-sHSP primers and Pfu genomic DNA.

The results of the agarose gel electrophoresis showed the following:

| Lane 1 | 100 bp ladder (Promega) |
| Lane 2 | PCR with normal Taq polymerase |
| Lane 3 | PCR with normal Taq polymerase and 1 μl of sHSP (final concentration) |
| Lane 4, 5 | PCR with Taq incubated at 50° C. 20 hours with 1 μl of dH$_2$O |
| Lane 6, 7 | PCR with Taq incubated with sHSP at 50° C. 20 hours |

Figure 5:
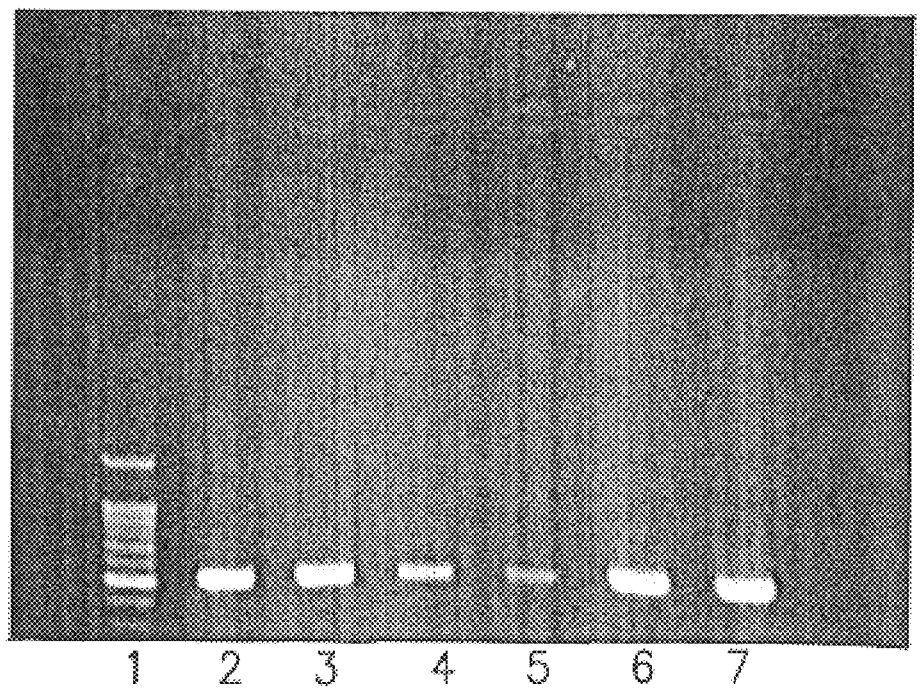
FIG. 5 demonstrates the agarose gel electrophoresis (1%) of the protection of Taq polymerase by the *Pyrococcus furiosus*-sHSP.

FIG. 5 shows the results of the agarose gel electrophoresis.

EXAMPLE 6
Limitation of the Polymerase Molecules to Carry Out PCR Products

This procedure is carried out by the following steps.
1. Taq polymerase is diluted into several dilutions.
2. The diluted Taq polymerase is incubated with and without small heat shock protein.
3. The PCR process is performed.
4. A comparison is made of the PCR products from Taq polymerase incubated with and without the sHSP to establish the lowest dilution that carries out the PCR products.

EXAMPLE 7
Limitation of the Polymerase Molecule to Sequence PCR Product

This procedure is carried out by the following steps.
1. Thermosequenase used for sequencing PCR products is diluted into several dilutions.
2. The enzyme from step 1 is incubated with and without sHSP.
3. The PCR process is performed.
4. An automated DNA sequencer is employed to carry out the sequencing.
5. The sequencing peaks as a result from the enzyme incubated with and without sHSP are compared.

EXAMPLE 8
Effect of Pfu-sHSP on Taq Polymerase Concentration in PCR Reaction

Figure 6:
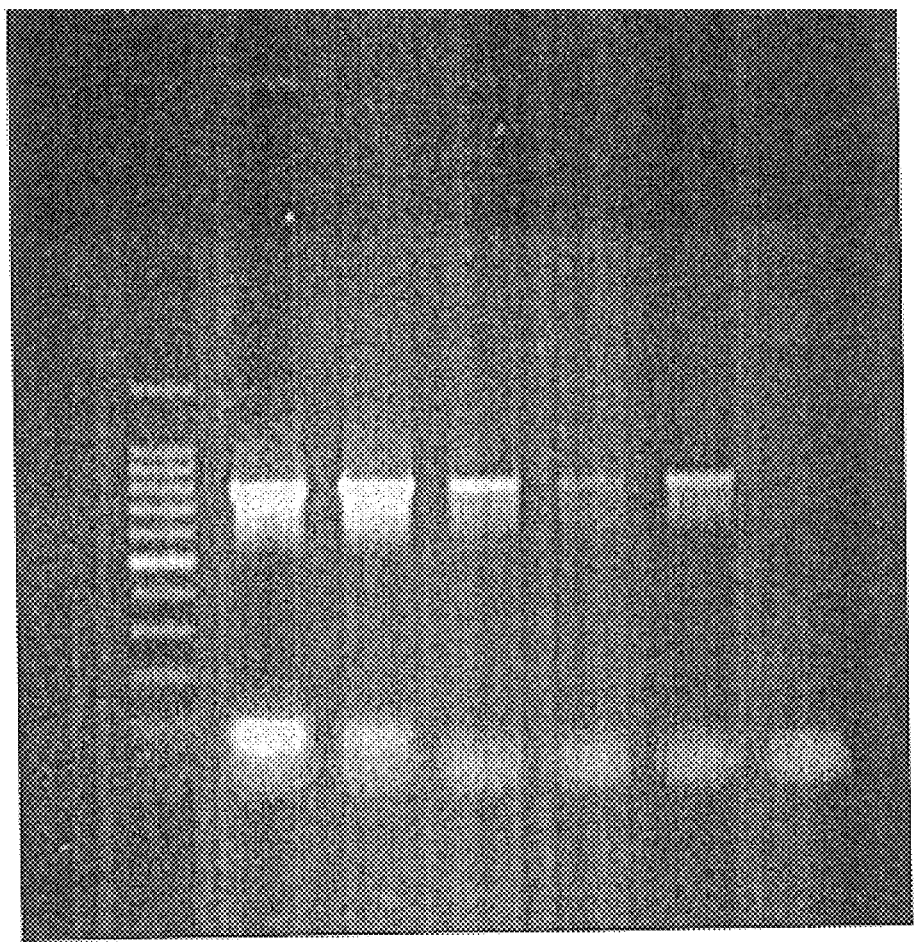
FIG. 6 depicts an electrophoretic gel (1% agarose) showing the effect of Pfu-sHSP on Taq polymerase concentration in PCR reaction.
Figure 7:
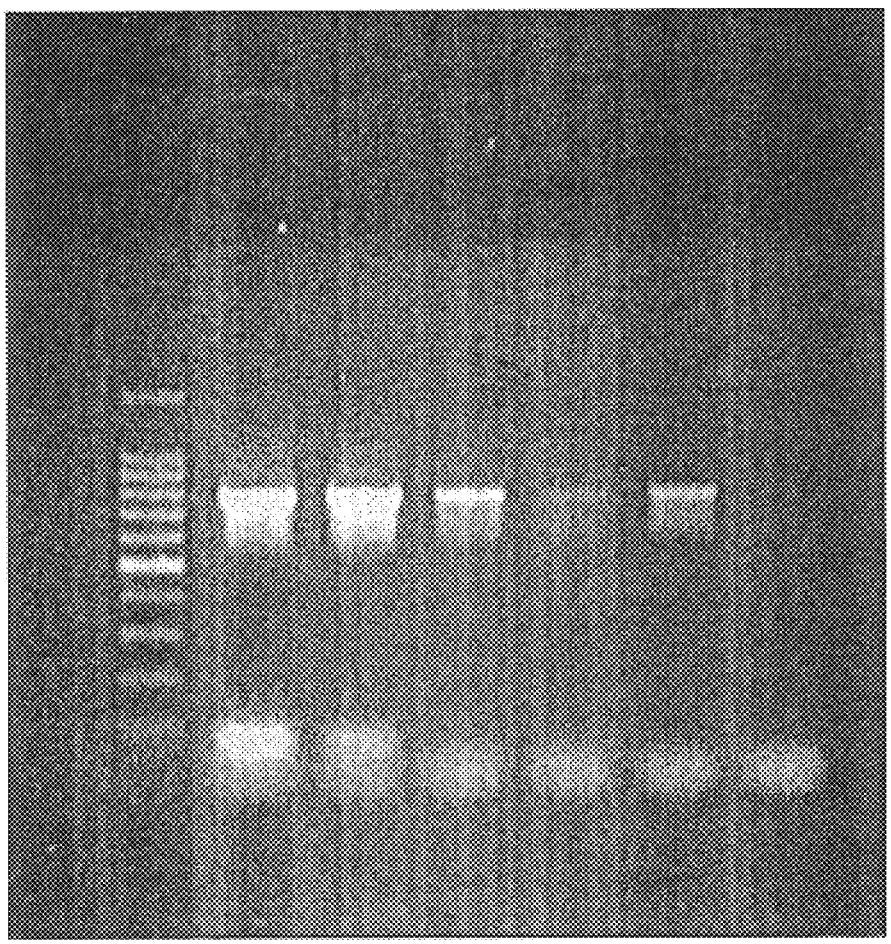
FIG. 7 depicts another electrophoretic gel (1% agarose) showing the effect of Pfu-sHSP on Taq polymerase concentration in PCR reaction.
Figure 8:
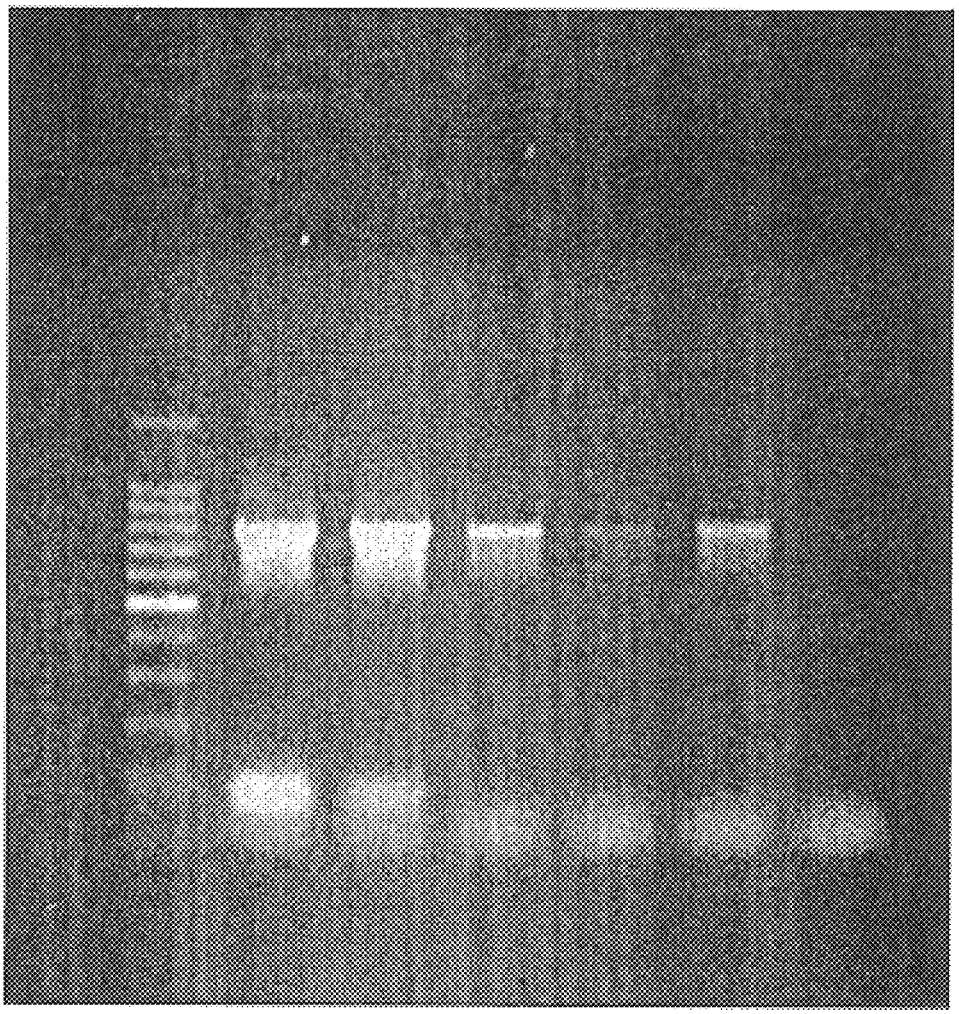
FIG. 8 depicts yet another electrophoretic gel (1% agarose) showing the effect of Pfu-sHSP on Taq polymerase concentration in PCR reaction.

The effect of Pfu-sHSP on concentration of Taq polymerase (Fisher Scientific) in a PCR reaction medium was assessed in three separate experiments, whose results are shown in the electrophoretic gels depicted in FIGS. 6–8.

FIG. 6 depicts an electrophoretic gel (1% agarose) showing the effect of Pfu-sHSP on Taq polymerase concentration in PCR reaction, at an sHSP concentration of 0.2 μg/μl. The respective lanes 1–7 shown in the figure are as follows:

| Lane 1 | 100 bp marker | |
| Lane 2 | 0.025 U/μl | +sHSP |
| Lane 3 | 0.025 U/μl | −sHSP |
| Lane 4 | 0.005 U/μl | +sHSP |
| Lane 5 | 0.005 U/μl | −sHSP |
| Lane 6 | 0.0025 U/μl | +sHSP |
| Lane 7 | 0.0025 U/μl | −sHSP |

FIG. 7 depicts another electrophoretic gel (1% agarose) showing the effect of Pfu-sHSP on Taq polymerase concentration in PCR reaction, at an sHSP concentration of 0.2 μg/μl. The respective lanes 1–7 shown in the figure are as follows:

| Lane 1 | 100 bp marker | |
| Lane 2 | 0.025 U/μl | +sHSP |
| Lane 3 | 0.025 U/μl | −sHSP |
| Lane 4 | 0.005 U/μl | +sHSP |
| Lane 5 | 0.005 U/μl | −sHSP |
| Lane 6 | 0.0025 U/μl | +sHSP |
| Lane 7 | 0.0025 U/μl | −sHSP |

FIG. 8 depicts yet another electrophoretic gel (1% agarose) showing the effect of Pfu-sHSP on Taq polymerase concentration in PCR reaction, at an sHSP concentration of 0.2 μg/μl. The respective lanes 1–7 shown in the figure are as follows:

| Lane 1 | 100 bp marker | |
| Lane 2 | 0.025 U/μl | +sHSP |
| Lane 3 | 0.025 U/μl | −sHSP |
| Lane 4 | 0.005 U/μl | +sHSP |
| Lane 5 | 0.005 U/μl | −sHSP |
| Lane 6 | 0.0025 U/μl | +sHSP |
| Lane 7 | 0.0025 U/μl | −sHSP |

The results are consistent in the respective experimental runs, and show that the presence of Pfu-sHSP in the PCR reaction volume was associated with a higher concentration of Taq polymerase in the reaction medium than in the corresponding reaction volumes in which the Pfu-sHSP heat shock protein was not present.

The results thereby demonstrate the advantage of utilizing a heat shock protein in accordance with the invention, in PCR operations. The present invention contemplates a PCR kit including a heat shock protein component for use in the PCR reaction medium to resist aggregation and precipitation of the polymerase component of the reaction mixture. The PCR kit in a specific embodiment may therefore include PCR primers, Taq polymerase, deoxyribonucleoside triphosphates and an HSP. Alternatively, the PCR kit may include an HSP together with at least one other of the components specified in the preceding sentence.

The foregoing results evidence the utility of the inventive method for stabilizing a protein solution including a first protein, against heat-mediated agglomeration of such first protein in the solution, by incorporating in the solution a heat shock protein that is non-endogenous with respect to the first protein.

The clear effects of Pfu-sHSP on protein stabilization and the increased thermotolerance it confers on *E. coli* reflect the mechanisms of its action in vivo. Protein stabilization is consistent with the maintenance of solubility of proteins, thereby promoting refolding and assembly. It is highly unexpected and fundamentally surprising that a component of the adaptive response of an archaeum growing at 100° C., such as *P. furiosus*, can enhance the heat resistance of organisms (e.g., *E. coli*) growing at much lower temperatures. The invention therefore embodies a substantial advance in the art of heat shock proteins, implicating a wide variety of applications in which such heat shock proteins confer enhanced thermotolerance, survivability and utility in the context of supraordinary thermal exposure conditions.

The disclosures of all references cited herein are hereby incorporated herein in their respective entireties.

While the invention has been described herein with reference to various illustrative features, aspects, and embodiments, it will be appreciated that the utility of the invention is not thus limited, but rather extends to and encompasses other variations, modifications and other embodiments, as will readily suggest themselves to those of ordinary skill in the art. Accordingly, the invention is to be broadly interpreted and construed as including such other variations, modifications and other embodiments, within the spirit and scope of the invention as hereinafter claimed.

What is claimed is:

1. The protein encoded by the nucleic acid comprising SEQ ID NO. 1.

2. A protein comprising the amino acid sequence of SEQ ID NO. 2.

3. A composition comprising the protein of claim 1.

4. A composition comprising the protein of claim 2.

5. A method of protecting and extending the durability of a recombinant DNA polymerase, comprising the steps of:
   (a) adding a heat shock protein comprising the amino acid sequence of SEQ ID NO. 2 to a buffer solution containing said polymerase;
   (b) incubating the solution at elevated temperature for a predetermined time;
   (c) adding components necessary for polymerase chain reaction;
   (d) thermocycling said reaction to produce product from amplification of genomic deoxyribonucleic acid; and
   (e) examining said product by gel electrophoresis.

6. A method of maintaining proteins in solution, comprising the steps of:
   (a) adding a heat shock protein comprising the amino acid sequence of SEQ ID NO. 2 to the solution;
   (b) elevating the temperature of the solution; and
   (c) measuring the enzymatic activity by absorbance.

7. A PCR kit, comprising a protein as in claim 1.

8. A PCR kit, comprising a protein as in claim 2.

9. A method of enhancing the stability of Taq polymerase in a PCR operation, comprising conducting said PCR operation in the presence of a heat shock protein comprising the amino acid sequence of SEQ ID NO. 2.

10. The method of claim 9, wherein said heat shock protein comprises a Pfu-sHSP heat shock protein.

11. The method of claim 9, wherein said heat shock protein is encoded by nucleic acid comprising SEQ ID NO. 1.

12. A composition comprising (i) a biological component and (ii) a heat shock protein comprising the amino acid sequence of SEQ ID NO. 2.

13. The composition of claim 12, wherein said biological component comprises a material selected from the group consisting of biological cells, and fractions and components thereof.

14. The composition of claim 12, wherein said biological component comprises an enzyme.

15. The composition of claim 12, wherein said biological component comprises a microbial culture.

16. The composition of claim 12, comprising a solution.

17. The composition of claim 16, wherein the biological component comprises a protein, and the heat shock protein comprising the amino acid sequence of SEQ ID NO. 2 is present in an effective amount to enhance resistance of the protein to aggregation and/or precipitation upon heat exposure of the composition.

18. The composition of claim 12, wherein said heat shock protein comprises a Pfu-sHSP heat shock protein.

19. The composition of claim 12, wherein said heat shock protein is encoded by nucleic acid comprising SEQ ID NO. 1.

20. A PCR kit including PCR primers, Taq polymerase, deoxyribonucleoside triphosphates and a heat shock protein comprising the amino acid sequence of SEQ ID NO. 2.

21. The PCR kit of claim 20, wherein said heat shock protein comprises a Pfu-sHSP heat shock protein.

22. The PCR kit of claim 20, wherein said heat shock protein is encoded by nucleic acid comprising SEQ ID NO. 1.

23. A method of stabilizing a protein solution, including a first protein therein, against heat-mediated agglomeration of said first protein in the solution, comprising incorporating in the solution a heat shock protein that is non-endogenous with respect to said first protein, wherein said heat shock protein comprises the amino acid sequence of SEQ ID NO. 2.

24. The method of claim 23, wherein said heat shock protein comprises a Pfu-sHSP heat shock protein.

25. A PCR kit, comprising an sHSP20 heat shock protein, and optionally including at least one component selected from the group consisting of(i) PCR primers, (ii) a polymerase effective for PCR and (iii) deoxyribonucleoside triphosphates.

26. A method of conducting a PCR reaction by use of a PCR kit including an sHSP20 heat shock protein, and optionally including at least one component selected from the group consisting of (i) PCR primers, (ii) a polymerase effective for PCR and (iii) deoxyribonucleoside triphosphates, said method comprising conducting said PCR reaction in the presence of said sHSP20 heat shock protein from said PCR kit.

* * * * *

UNITED STATES PATENT AND TRADEMARK OFFICE
CERTIFICATE OF CORRECTION

PATENT NO.   : 6,579,703 B2
DATED         : June 17, 2003
INVENTOR(S)  : Robb et al.

It is certified that error appears in the above-identified patent and that said Letters Patent is hereby corrected as shown below:

Column 7,
Line 30, "pSJS 1240" should be -- pSJS1240 --

Column 15,
Line 35, delete "The" and insert -- An isolated --
Line 35, delete "the nucleic acid comprising"
Line 38, delete "A" and insert -- An isolated --

Column 16,
Line 63, delete "including" and insert -- comprising --

Signed and Sealed this

Twenty-first Day of October, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 712
<212> TYPE: DNA
<213> ORGANISM: Pyrococcus furiosus

<400> SEQUENCE: 1

```
tctttttttgg agtattttg attgttcggt aaattctact cttatcgaaa atatttataa      60
accccaaata atttaataac taatggtaac caaaagtggg aggggtgag agagatggtg      120 aggagaataa gaagatggga catatgggat ccattcgacc taataaggga aatacaagag      180
gaaattgatg caatgttcga tgaattcttc agcaggccaa ggctctggac ttacagaagg      240
tggagcgagc cagcaatgta tgaggagaga gtaggagaag tctggagaga gccattcgtt      300
gatatctttg acaacggaga tgagtttgta atcacggcag agcttccagg agtgagaaaa      360
gaagacatca aagtgagggt tacagaggat acagtataca ttgaggccac agttaagagg      420
gagaaagaat tagaaagaga aggagcagtg agaatagaga gatactttac agggtataga      480
agagccatca ggcttccaga agaagttatt ccagagaagg caaaggccaa gtacaacaac      540
ggagtgcttg agatcagagt tccaaagaag cacccaacaa agaaggagag tgaaggattc      600
gaagttaaag ttgaatagct ttagtaccct tctttcttga ttatttggaa atattttgg      660 aggtattggt tctattatca attaattcct tttattttaa aatccttgga tc             712
```

<210> SEQ ID NO 2
<211> LENGTH: 167
<212> TYPE: PRT
<213> ORGANISM: Pyrococcus furiosus

<400> SEQUENCE: 2

```
Met Val Arg Arg Ile Arg Arg Trp Asp Ile Trp Asp Pro Phe Asp Leu
1               5                   10                  15

Ile Arg Glu Ile Gln Glu Glu Ile Asp Ala Met Phe Asp Glu Phe Phe
            20                  25                  30

Ser Arg Pro Arg Leu Trp Thr Tyr Arg Arg Trp Ser Glu Pro Ala Met
        35                  40                  45

Tyr Glu Glu Arg Val Gly Glu Val Trp Arg Glu Pro Phe Val Asp Ile
    50                  55                  60

Phe Asp Asn Gly Asp Glu Phe Val Ile Thr Ala Glu Leu Pro Gly Val
65                  70                  75                  80
```

```
Arg Lys Glu Asp Ile Lys Val Arg Val Thr Glu Asp Thr Val Tyr Ile
                85              90                  95

Glu Ala Thr Val Lys Arg Glu Lys Glu Leu Glu Arg Glu Gly Ala Val
            100             105             110

Arg Ile Glu Arg Tyr Phe Thr Gly Tyr Arg Arg Ala Ile Arg Leu Pro
        115             120             125

Glu Glu Val Ile Pro Glu Lys Ala Lys Ala Lys Tyr Asn Asn Gly Val
        130             135             140

Leu Glu Ile Arg Val Pro Lys Lys His Pro Thr Lys Lys Glu Ser Glu
145             150             155             160

Gly Phe Glu Val Lys Val Glu
                165

<210> SEQ ID NO 3
<211> LENGTH: 27
<212> TYPE: DNA
<213> ORGANISM: synthetic construct

<400> SEQUENCE: 3
gccatggtga ggagaataag aagatgg                                          27

<210> SEQ ID NO 4
<211> LENGTH: 34
<212> TYPE: DNA
<213> ORGANISM: synthetic construct

<400> SEQUENCE: 4
actcgagcta ttcaacttta acttcgaatc cttc                                  34
```